(12) United States Patent
Baecke et al.

(10) Patent No.: US 7,384,237 B2
(45) Date of Patent: Jun. 10, 2008

(54) FAN UNIT FOR A VENTILATOR

(76) Inventors: Martin Baecke, Lindenstr. 7, Dessau (DE) 06847; Peter Hartung, Fuchsweg 6, Halle/Saale (DE) 06120

( * ) Notice: Subject to any disclaimer, the term of this patent is extended or adjusted under 35 U.S.C. 154(b) by 433 days.

(21) Appl. No.: 11/132,540

(22) Filed: May 19, 2005

(65) Prior Publication Data
US 2005/0210622 A1    Sep. 29, 2005

Related U.S. Application Data

(63) Continuation of application No. PCT/DE03/03590, filed on Oct. 29, 2003.

(51) Int. Cl.
*F04D 29/44* (2006.01)
(52) U.S. Cl. .................. 415/205; 417/423.1
(58) Field of Classification Search ............... 415/205, 415/120, 71, 73, 75, 224.5; 417/423.7
See application file for complete search history.

(56) References Cited

U.S. PATENT DOCUMENTS

| 5,335,654 | A | 8/1994 | Rapoport |
| 5,740,795 | A | 4/1998 | Brydon |
| 6,960,854 | B2 * | 11/2005 | Nadjafizadeh et al. ...... 415/203 |
| 2002/0057967 | A1 | 5/2002 | Eimer et al. |
| 2003/0168064 | A1 | 9/2003 | Daly et al. |

FOREIGN PATENT DOCUMENTS

| DE | 44 25 300 | 1/1996 |
| DE | 195 10 553 | 9/1996 |
| DE | 198 49 571 | 5/2000 |
| DE | 691 32 030 | 10/2000 |
| DE | 101 18 968 | 10/2002 |
| EP | 0 872 643 | 10/1998 |

(Continued)

OTHER PUBLICATIONS

Avram R. Gold, MD; Alan R. Schwartz, MD, "The Pharyngeal Critical Pressure," Chest/110/4, Oct. 1996, pp. 1077-1088.

(Continued)

*Primary Examiner*—Richard A. Edgar
(74) *Attorney, Agent, or Firm*—King & Schickli, PLLC

(57) ABSTRACT

The invention relates to fan units for ventilators, in particular for CPAP-apparatus. The fan units comprise a housing, a motor having a stator and a rotor, with the stator being affixed to the housing, and an impeller affixed to the rotor. According to an embodiment the motor is positioned in the suction area of the impeller and the housing forms a suction channel extending helically about the motor axis and being arranged such that the sucked air is accelerated in the direction of rotation of the motor. According to another embodiment the housing in the proximity of the fixtures of the motor is formed such that the housing acts as spring element itself. According to another embodiment a tissue is provided in the fan unit through which the air flows after its compression by the impeller. According to another embodiment a suction port is affixed on the outside of the housing of the fan unit, and a tissue for sound damping is provided in the transition region between the suction port and a suction channel formed by the housing.

12 Claims, 1 Drawing Sheet

FOREIGN PATENT DOCUMENTS

| | | |
|---|---|---|
| EP | 0 934 723 | 8/1999 |
| EP | 0 612 257 | 6/2000 |
| FR | 2 663 547 | 12/1991 |
| FR | 2 763 367 | 11/1998 |
| GB | 2 209 474 | 5/1989 |
| WO | WO 94/23780 | 10/1994 |
| WO | WO 99/24099 | 5/1999 |
| WO | WO 00/24446 | 5/2000 |

OTHER PUBLICATIONS

Alan R. Schwartz; James A. Rowley; David C. Thut; Solbert Permutt; Philip L. Smith, "Structural Basis for Alterations in Upper Airway Collapsibility," Sleep, 19(10), pp. S184-S188.

International Search Report from corresponding International patent application No. PCT/DE2003/03590.

* cited by examiner ized by *reference*.

FAN UNIT FOR A VENTILATOR

CROSS REFERENCE TO RELATED CO-PENDING APPLICATIONS

This application is a continuation of international application number PCT/DE03/03590 (publication number: WO 2004/046556 A2) filed on Oct. 29, 2003 and entitled FAN UNIT FOR A VENTILATOR and claims the benefit of the above-mentioned international application and the corresponding German national patent application number 102 53 937.5-09 filed on Nov. 19, 2002 and entitled LÜFTEREINHEIT FÜR EIN BEATMUNGSGERÄT the contents of which are expressly incorporated herein by reference.

FIELD OF THE INVENTION

The invention relates to fan units for ventilators, in particular for ventilators for performing the CPAP-therapy. Such fan units comprise a housing, a motor and an impeller. Inventive fan units are applied in known CPAP-apparatus.

BACKGROUND OF THE INVENTION

Radial fans as well as impellers for radial fans are, for example, known from "Strömungsmaschinen" by Klaus Menny, $3^{rd}$ Edition, B. G. Teubner Stuttgart, 2000. In this application the terms "fan", "compressor", "ventilator" or "blower" are used as synonyms. Radial fans are, inter alia, used in ventilators, in particular in CPAP-apparatus.

The CPAP-therapy (continuous positive airway pressure) was developed for the treatment of apneas and is described in Chest. Volume No. 110, pages 1077-1088, October 1996 and in Sleep, Volume No. 19, pages 184-188. A CPAP-apparatus generates, preferably by means of a high-speed, single-stage radial compressor, a positive overpressure up to approximately 30 mbar and administers the same to the respiratory tract of the patient via a hose and a nose mask. This positive pressure is to ensure that the upper respiratory tract remains fully opened during the whole night, so that no apneas will occur (DE 198 49 571 A1).

Suppliers of compressors suited for CPAP-apparatus are, for example, AMETEK, ROTRON, PAPST, ebm, Micronel, Telemeter Electronic. Complete CPAP-apparatus are, for example, distributed by MAP, Weinman or ResMed. It is common that the fan unit is placed in a sound-damping and sound-absorbing box inside the CPAP-apparatus.

Barriers for the use of compressors are primarily the construction size, the weight and the noise development. The construction size and the weight of portable CPAP-apparatus are presently around 5.5 liters and 2.5 kg. The noise development should not exceed 30 dB, as the patients are to have a relaxing sleep beside the apparatus. In order to keep the noise development of known CPAP-fans small, the impeller and the blow-off port of known radial CPAP-fans are offset against each other, i.e. they are not arranged in a plane. A further reduction of the construction size and the weight, e.g. by using smaller compressors, would be desirable.

A maximum air volume of 200 l/min and a maximally achievable pressure of at least 25 mbar (2500 Pa) in the face mask are required for CPAP-apparatus. Pressures around 15 mbar must still allow the conveyance of at least 150 l/min. These requirements apply to conventional respiratory hoses with inner diameters around 20 mm.

Moreover required is a running smoothness, i.e. a small noise development. The radial compressors primarily used so far have to be operated at very high speeds, which results in disturbing whistling sounds.

The company Hörnell developed a welder mask comprising a radial fan from Papst. The fan is fastened on the welder's back by means of a belt. A hose having a diameter of approximately 20 to 30 mm leads from the fan into the top of the welder mask. The fan supplies the welder with 160 liters of fresh air per minute and thus also provides for sufficient cooling.

SUMMARY OF THE INVENTION

According to an embodiment of the invention a fan unit for a ventilator is provided. The fan unit comprises a housing, a motor and an impeller. The housing defines a suction channel as part of a suction area. The motor having a stator and a rotor. The stator is affixed to the housing. The suction area extends helically about the motor axis. The suction area being arranged such that the sucked air is accelerated in the direction of rotation of the motor. The impeller being affixed to the rotor, the motor being positioned in the suction area of the impeller.

According to another embodiment of the invention another fan unit for a ventilator is provided. The fan unit comprises a housing, a motor and an impeller. The housing has fixtures. The housing being formed in the proximity of the fixtures such that it acts as a spring element itself. The motor is comprised of a stator and a rotor. The stator being affixed to the fixtures and the impeller is affixed to the rotor.

According to a further embodiment of the invention a fan unit for a ventilator is provided. The fan unit comprises a housing, a motor, an impeller and a tissue. The motor has a stator and a rotor. The stator is affixed to the housing and the impeller affixed to the rotor. After its compression by the impeller, the air flows through a tissue.

According to yet a further embodiment of the invention a fan unit for a ventilator. The fan unit comprises a housing, a motor and an impeller. The housing forms a suction channel. The motor has a stator affixed to the housing and a rotor. The impeller is affixed to the rotor. A suction port is affixed on the outside of the housing. A tissue for sound damping is fixed in the transition region between the suction port and the suction channel.

The accommodation of the motor in the suction area reduces the construction size of the fan unit.

A helical suction channel reduces the noise delivered by the fan through a suction port.

A reduction of the relative speed of the suction air with respect to the inner ends of the impeller blades reduces the noise development on the impeller and may be achieved by arranging the suction channel about the motor axis in a helical manner.

The motor cooling is improved due to the fact that the motor forms an inner wall of the suction channel and a suction ring. The formation of a suction ring results from the arrangement of the blow-off port between the suction spiral and the impeller so as to achieve a small construction height without any excessive noise development.

If the suction channel extends annularly about the rotational axis of the motor over an angle sector of 250 to 330° the available space is optimally utilized.

By appropriately constructing the housing it is achieved that as little as possible structure-borne noise is transferred from the motor to the housing. Structure-borne noise is caused, for example, by running noises in the bearings between the stator and the rotor of the motor.

Another noise reduction may be obtained by providing tissue in the transition regions between the suction port and the suction channel, between the suction channel and the suction ring or between the pressure space and the blow-off port.

By defining the partition wall between the suction channel and the pressure space as a generated surface of a truncated cone the cross-sectional area between the pressure space and the suction channel in a plane comprising the rotational axis of the motor is divided into approximately equal parts between the pressure space and the suction channel. Thus, the suction channel is provided with a cross-section that is large enough to allow a sufficiently high flow with a small noise development.

The grids take care of uncoupling the acoustic resonance spaces, in particular the suction channel, the pressure space and the respiratory hose affixed to the blow-off port. This eliminates low-frequency resonances, which facilitates the structure of the sound-absorbing box inside the CPAP-apparatus in which the fan unit is usually mounted, so that the sound-damping and sound-absorbing box can be constructed in a more compact manner so as to take up a smaller volume.

Preferred embodiments of the invention are subject matter of the dependent claims.

BRIEF DESCRIPTION OF THE DRAWINGS

Preferred embodiments of the invention will hereinafter be explained in more detail with reference to the enclosed drawings, wherein like numerals represent like parts.

DETAILED DESCRIPTION OF THE INVENTION

Figure 1:
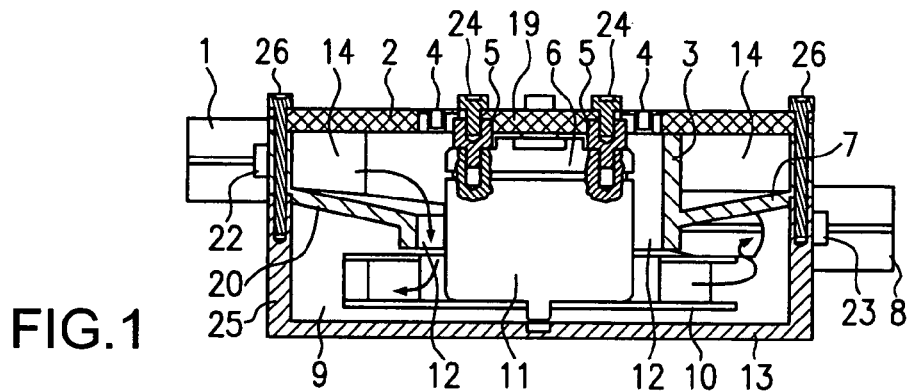
FIG. 1 shows a section through the motor axis of a fan unit according to the invention.

FIG. 1 shows a fan unit according to the invention. This fan unit comprises a suction port 1, a housing with a housing bottom 13, insert member 20 and lid 2, a motor with stator 6 and rotor 11, an impeller 10 and a blow-off port 8. The stator of the motor is affixed to the housing lid 2 by means of elements 5. Moreover, a spring element 4 is integrated in the lid. The portion being spring-mounted with respect to the outer edge of the lid is designated with reference numeral 19. The insert member 20 forms a part of the outer wall 21 of the housing, a partition wall 7 between a helical suction channel 14 and a pressure space 9 as well as the outer limitation of a suction ring 12. The housing bottom 13 substantially forms the limitation of the pressure space 9, in particular a portion of the outer wall 25. The rotor 11 rotates the impeller 10, with said impeller being directly affixed to the rotor of the motor 11, as is shown in FIG. 1.

For the sake of clearness no grids are illustrated in FIG. 1. Elements 5 may be spring elements and/or damping elements. According to one embodiment the elements 5 may be made of rubber which is both resilient and dampening. A particularly well dampening synthetic material is Viton.

Figure 2:
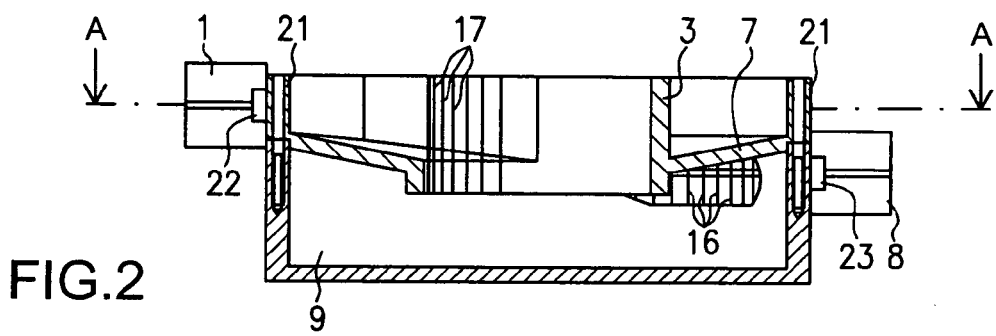
FIG. 2 shows the same section as in FIG. 1, but without lid, motor and impeller.

For the sake of clarity the section of FIG. 1 is once more illustrated in FIG. 2, however, without showing the impeller 10, the motor 5, 6 and the housing lid 2. In addition to the objects shown in FIG. 1 grids 16 and 17 are symbolically illustrated by bars parallel to the motor axis.

Figure 3:
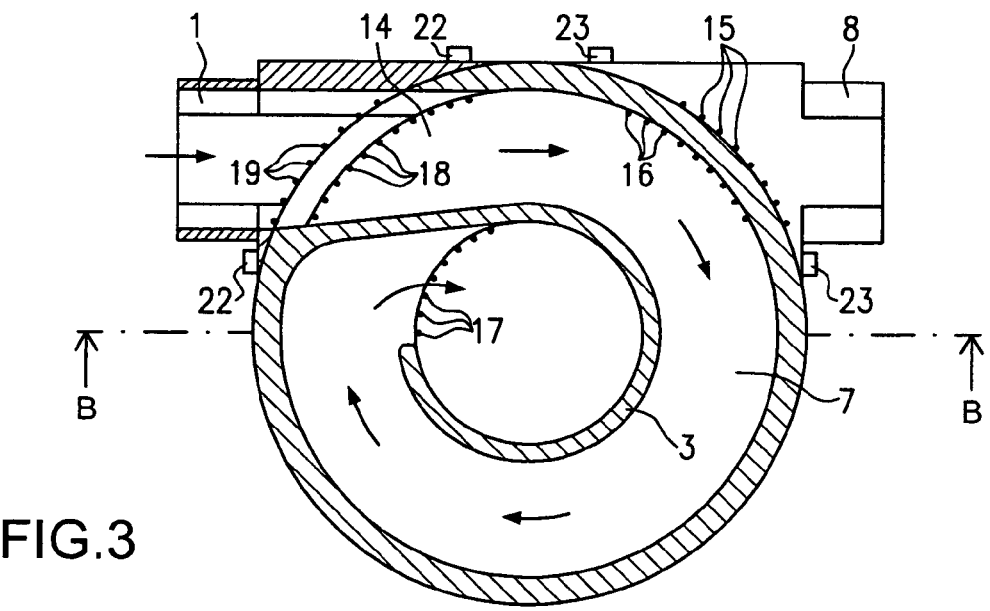
FIG. 3 shows a section perpendicular to the motor axis of a fan unit according to the invention.

FIG. 3 shows a section along line A-A in FIG. 2. In FIG. 3, again, the grids 16 and 17 are illustrated as bars parallel to the motor axis. Moreover, additional grids 15, 18 and 19 are drawn in analogously. Finally, the cutting plane B-B for FIG. 2 is shown in FIG. 3.

Figure 4:
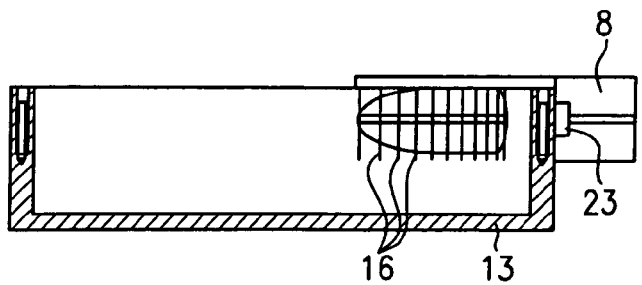
FIG. 4 shows a section through the bottom of a housing of a fan unit according to the invention.

FIG. 4 shows the housing bottom 13 with the blow-off port 8 screwed thereto.

In the embodiment illustrated in FIGS. 1 to 4 the suction port 1 is screwed to insert member 20 by means of screws 22. Similarly, the blow-off port 8 is screwed to the housing bottom 13 by means of screws 23. Lid 2 and insert member 20 are connected with the housing bottom 13 by means of screws 26. Elements 5 are affixed to the lid 2 by means of screws 24.

Persons skilled in the art will be aware that the suction port 1, lid 2, blow-off port 8, housing bottom 13 and insert member 20 required to manufacture the fan unit according to the invention are fabricated, for reasons of costs, in large numbers of pieces by means of injection molding. With this fabrication method it is an advantage, however, that the housing bottom 13 is integrally produced with the blow-off port 8 and the insert member 20 is integrally produced with suction port 1 as one piece so as to save the steps of attaching both ports by means of screws. Also, the outer edge of lid 2, the spring element 4 and the spring-mounted portion of lid 19 are preferably made of the same material.

During the operation air is sucked in through the suction port 1. The air subsequently enters the suction channel 14. As can be seen in FIG. 3, the suction channel 14 extends in a helical manner about the motor axis over an angle sector of approximately 250 to 330°. The suction channel is limited by the ring wall 3 in the inside, lid 2 at the top, partition wall 7 at the bottom and outer wall 21 on the outside. The area in which the ring wall 3 extends in a circular manner may be used to define the aforementioned angle sector of 250 to 330°. In another definition the circular shape of the outer wall 21 may be defined, i.e. 330° minus the transition region in which the grid 18 is located.

From the suction channel 14 the sucked air enters the suction ring 12. Suction channel and suction ring are together also designated as suction area. The inner limitation of the suction ring is defined by the rotor of the motor, and the outer limitation is defined by the ring wall 3. The flow of sucked air past the rotor of the motor improves the cooling thereof. Moreover, the helical suction of air in the direction of rotation of the motor through the suction channel, and the air skimming along the rotor of the motor, make the air accelerate in a rotational direction, so that the relative speed between the blades of the impeller 10 and the sucked air is reduced. This reduces the development of noise. Thus, the air enters from the suction ring into the impeller 10 and is pressed by the blades thereof and by the centrifugal force towards the outside into the pressure space 9. From the pressure space the air then flows into the blow-off port 8 and further through a respiratory hose to a patient. In the transition region between the pressure space and the blow-off port grids 15 and 16 may, again, be disposed.

As was mentioned above, the impeller 10 and the opening toward the blow-off port 8 must not be disposed on the same height so as to keep the noise development small. In the embodiment as illustrated the suction port, the blow-off port and the impeller are about equally high. As the outer wall 25 of the housing bottom is about as high as the impeller and the blow-off port together, while the outer wall 21 of the insert member is only as high as the suction port, the outer wall 25 of the housing bottom is approximately twice as high as the outer wall 21 of the insert member. If the partition wall 7 extended in a plane perpendicularly to the motor axis, the cross-section of the suction channel 14 in a plane comprising the motor axis would clearly be smaller than the cross-section of the pressure space, so that the suction channel 14 forms too high an air resistance. For distributing the cross-sectional areas between the pressure space and the suction channel more uniformly the partition wall 7 defines the generated surface of a truncated cone.

Grids 15 have proved to be most effective for reducing or avoiding noise. Nearly equally effective are grids 16, less effective are grids 17 and the least effective are grids 18 and 19. If grids 15 and 17 are installed, grids 18 or 19 hardly reduce the noise development any further. As the position of grids 15 has proved to be the most effective one, a particularly fine-meshed grid or two grids placed on top of each other may be used at this position.

The grids may be made of metal or a synthetic material. Loose cotton wool, wool, filter fleeces, molded bodies made of metallic or synthetical knitted fabric, as are known, for example, in connection with pot scrapers, or sieves may be used instead of the grids. The generic term tissue is used for these objects. Advantageously, grids and sieves may be fabricated with the housing by injection molding in one working cycle. As compared with loose cotton wool, wool or filter fleeces, molded bodies, sieves or grids have the advantage that no fibers will become loose.

In the foregoing, the invention was explained in more detail by means of preferred embodiments. It is, however, obvious for a person skilled in the art that various alterations and modifications may be made without departing from the spirit of the invention. Therefore, the scope of protection is defined by the following claims and their equivalents.

LIST OF REFERENCE NUMERALS

1 suction port
2 lid
3 ring wall
4 integrated spring element
5 spring and/or damping elements
6 stator of the motor
7 partition wall
8 blow-off port
9 pressure space
10 impeller
11 rotor of the motor
12 suction ring
13 housing bottom
14 suction channel
15-18 grids
19 spring-mounted portion of the lid
20 insert member
21 outer wall of the insert member
22-24, 26 screws
25 outer wall of the bottom of the housing

What is claimed is:

1. A fan unit for a ventilator, comprising:
a housing defining a suction channel as part of a suction area;
a motor having a stator and a rotor, with the stator being affixed to the housing;
the suction area extending helically about the motor axis; the suction area being arranged such that the sucked air is accelerated in the direction of rotation of the motor and an impeller affixed to the rotor, the motor being positioned in the suction area of the impeller.

2. The fan unit according to claim 1, wherein the motor defines the inner limitation of a suction ring as part of the suction area and the housing defines the outer limitation of the suction ring.

3. The fan unit according to claim 2, wherein a tissue is fixed in the transition region between the suction channel and the suction ring.

4. The fan unit according to claim 1, wherein the motor partially projects into the suction channel and thus partially defines an inner wall of the suction channel.

5. The fan unit according to claim 1, wherein the suction channel extends about the rotational axis of the motor over an angle sector of 2500 to 3300 in an arc-shaped manner.

6. The fan unit according to claim 1, wherein the housing further comprises a pressure space through which the air flows after its compression by the impeller, wherein the pressure space is separated from the suction channel by a truncated-cone-shaped partition wall so that the cross-sections of the suction channel and the pressure space in a plane comprising the motor axis are approximately equally large.

7. The fan unit according to claim 1, wherein there is no plane perpendicular to the motor axis and simultaneously intersecting the blades of the impeller and the housing opening to a blow-off port.

8. The fan unit according to claim 1, wherein the housing in the proximity of the fixtures of the stator is formed such that it acts as a spring element itself.

9. The fan unit according to claim 8, wherein the spring element surrounds the fixtures in a circular form and the cross-section of the spring element in a plane comprising the motor axis is waved.

10. The fan unit according to claim 1, wherein the stator is affixed to the housing by means of spring and damping elements.

11. The fan unit according to claim 1, wherein a suction port is affixed on the outside of the housing and a tissue is fixed in the transition region between the suction port and the suction channel.

12. The fan unit according to claim 1, further comprising a tissue through which the air flows after its compression by the impeller.

* * * * *

UNITED STATES PATENT AND TRADEMARK OFFICE
CERTIFICATE OF CORRECTION

| | |
|---|---|
| PATENT NO. | : 7,384,237 B2 |
| APPLICATION NO. | : 11/132540 |
| DATED | : June 10, 2008 |
| INVENTOR(S) | : Baecke et al. |

It is certified that error appears in the above-identified patent and that said Letters Patent is hereby corrected as shown below:

Title Page; item (30); please insert;

Foreign Application Priority Data

Nov. 19, 2002   [DE] -------------------- 102 53 937.5

Signed and Sealed this

Twelfth Day of August, 2008

JON W. DUDAS
*Director of the United States Patent and Trademark Office*